United States Patent
Buholzer et al.

(10) Patent No.: US 8,048,637 B2
(45) Date of Patent: Nov. 1, 2011

(54) **DIAGNOSTIC COMPOSITION AND METHOD FOR THE DETECTION OF A *TRICHINELLA* INFECTION**

(75) Inventors: Patrik Buholzer, Winterthur (CH); Alex Raber, Zurich (CH); Paul Price, Zurich (CH); Daniel Zwald, Monthal (CH); Weldy Bonilla Pinschewer, Zurich (CH); Roger Marti, Ursen (CH); Jurg Weidmann, Winterthur (CH); Christoph Stamm, Stein am Rhein (CH)

(73) Assignee: Prionics AG, Schlieren (CH)

( * ) Notice: Subject to any disclaimer, the term of this patent is extended or adjusted under 35 U.S.C. 154(b) by 0 days.

(21) Appl. No.: 12/666,027

(22) PCT Filed: Jun. 29, 2007

(86) PCT No.: PCT/EP2007/005774
§ 371 (c)(1),
(2), (4) Date: Dec. 22, 2009

(87) PCT Pub. No.: WO2009/003497
PCT Pub. Date: Jan. 8, 2009

(65) Prior Publication Data
US 2010/0190182 A1 Jul. 29, 2010

(51) Int. Cl.
*G01N 33/53* (2006.01)
*G01N 33/532* (2006.01)
*G01N 33/531* (2006.01)
*G01N 33/533* (2006.01)
*A61K 38/00* (2006.01)

(52) U.S. Cl. ......... 435/7.1; 436/543; 436/544; 436/546; 530/300

(58) Field of Classification Search .................. None
See application file for complete search history.

(56) References Cited

U.S. PATENT DOCUMENTS
5,422,263 A * 6/1995 Zarlenga et al. ......... 435/252.33

FOREIGN PATENT DOCUMENTS
| WO | 94/17824 | | 8/1994 |
| WO | 96/30044 | | 10/1996 |
| WO | WO2006094665 | * | 9/2006 |
| WO | 2007/090960 | | 8/2007 |

OTHER PUBLICATIONS

Soh et al. Mol. BioSyst, 2006, 2, 128-131.*
Zarlenga ('02) et al International Journal of Parasitology 32 (2002) 1361-1370.*
Nielsen et al. J. immunoassay Immunochem 2001;22(3):183-201.*
Adams et al. J. Am. Chem. Soc. 2002, 124, 6063-6076.*
Definition of kit: a set of articles or equipment needed for a specific purpose. Oxford Dictionaries. http://oxforddictionaries.com/search?q=kit&view=uk, retrieved Dec. 10, 2010.*
Zhang, Gai-Ping et al.; "Development and evaluation of an immunochromatographic strip for trichinellosis detection;" Veterinary Parasitology; Elsevier Science; Amsterdam, Netherlands; vol. 137, No. 3-4; Apr. 30, 2006; pp. 286-293; XP005364351.
Denkers, Eric Y. et al.; "The Mouse Antibody Response to *Trichinella spiralis* Defines a Single, Immunodominant Epitope Shared by Multiple Antigens"; Journal of Immunology; The Williams and Wilkins Co., Baltimore, Maryland; vol. 144, No. 8; Apr. 15, 1990; pp. 3152-3159; XP002027466.
Dea-Ayuela, Marial et al.; "*Trichinella* antigens: a review;" Veterinary Research; Elsevier; Paris; Netherlands; vol. 30, No. 6; Nov. 1999; pp. 559-571; XP008069175.

* cited by examiner

*Primary Examiner* — Oluwatosin Ogunbiyi
(74) *Attorney, Agent, or Firm* — Rankin, Hill & Clark LLP

(57) ABSTRACT

A diagnostic composition to detect antibodies in a sample obtained from an animal or human being infected by *Trichinella*, comprising at least one peptide containing a series of amino acids that form a continuous or discontinuous epitope recognized by sera from pigs infected with *Trichinella*.

20 Claims, 9 Drawing Sheets

*Trichinella spiralis* newborn larvae-specific protein SS1 (AF331159)

```
1        10        20        30        40        50        60        70        80        90
MFISIIVILISLKTCIAQVATCKNDNDANVDWYFVYKPPNVLSSKILQSGVNPAWAASRANINQGAGHSIIRTMASFVVHHAQINVLAYSDDPPNLPPR
                                                                           (SEQ ID NO: 2) QINVLAYSDDPPNLPPR 100       110       120       130       140       150       160       170       180       190
NEKSKTKGVLLVNNAADEAAWFVHTVPNFLAYLNAYSWPPAETPKGHMFLCVSFNKAHLNSVGKAIRYQEPYVYANNLPAAILNQNMELFNLINGIDVR
NEKSKTKG                                                  (SEQ ID NO: 3) IRYQEPYVYANNLPAAILNQN 200       210       220       230       240       250       260       270       280       290
VTSFLAHETFATKSVQAVANIQAFGKHSKSFADMYARILRNRFAASIMVWSPADARSKSICKGQHKLQKITSIQLDGVQVSREADSAKWALIDGKNTVC 300       310       320       330
FTTNDYTATEKRTPGAAVCLENAGVYNAFRTAALNVEACNN
```

Fig. 1

*Trichinella spiralis* newborn larvae-specific protein SS2 (AF331160)

```
            20                  40                  60                  80
MHKITHKSIVSRHTFAVYLLVSGQKLQYIYIFICKMIRRLFQYTSMTFAWILLFLSAASPSLGAFECGVPHFKPYIWKSGRIVGGTDVRPHSHPWQIQLL
MHKITHKSIVSRHTFAVYLLVSGQK (SEQ ID NO 5)           (SEQ ID NO 6)  VGGTDVRPHSHPWQIQLL
           120                 140                 160                 180
KSETGGYSSLCGGSLVHFGKPSNGTRFVLTAAHCITTSNMYPRTSRFTVVTGAHNIKMHEKEKKRLPITSYYVQHWNPVMTTNDIALLRLAETVYYNEYT
KSETG
           220                 240                 260                 280
RPVCLPEPNEELTPGDICVVTGWGDTTENGTTSNTLKQVGVKIMKKGTCANVRSEVITFCAGAMEGGKDSCQGDSGGPLICKKNGKSVQFGVVSYGTGCA
           320                 340                 360                 380
RKGYPGVYAKVPSYVTWLNKAAKELENSPEGTVKWASKEDSPVDLSTASRPTNPYTGSRPTSPSSGSRPTYPSSGSRPTYPS
                              (SEQ ID NO:7)        (SEQ ID NO:8)
                       LSTASRPTNPYTGSRPTSPSSGSRP  PTYPSSGSRPTYPS
                                                  (SEQ ID NO:9)
                                                  PTYPSSGSRPTYPS
           420                 440                 460
SGSRPTYPYTGSRPTPQKPVFPSYQKYPPAVQKYIDSLPSGTQGTLEYTVTQNGVTTTTYYHFSK
SGSRPTYPYTG
SGSRP
```

Fig. 2

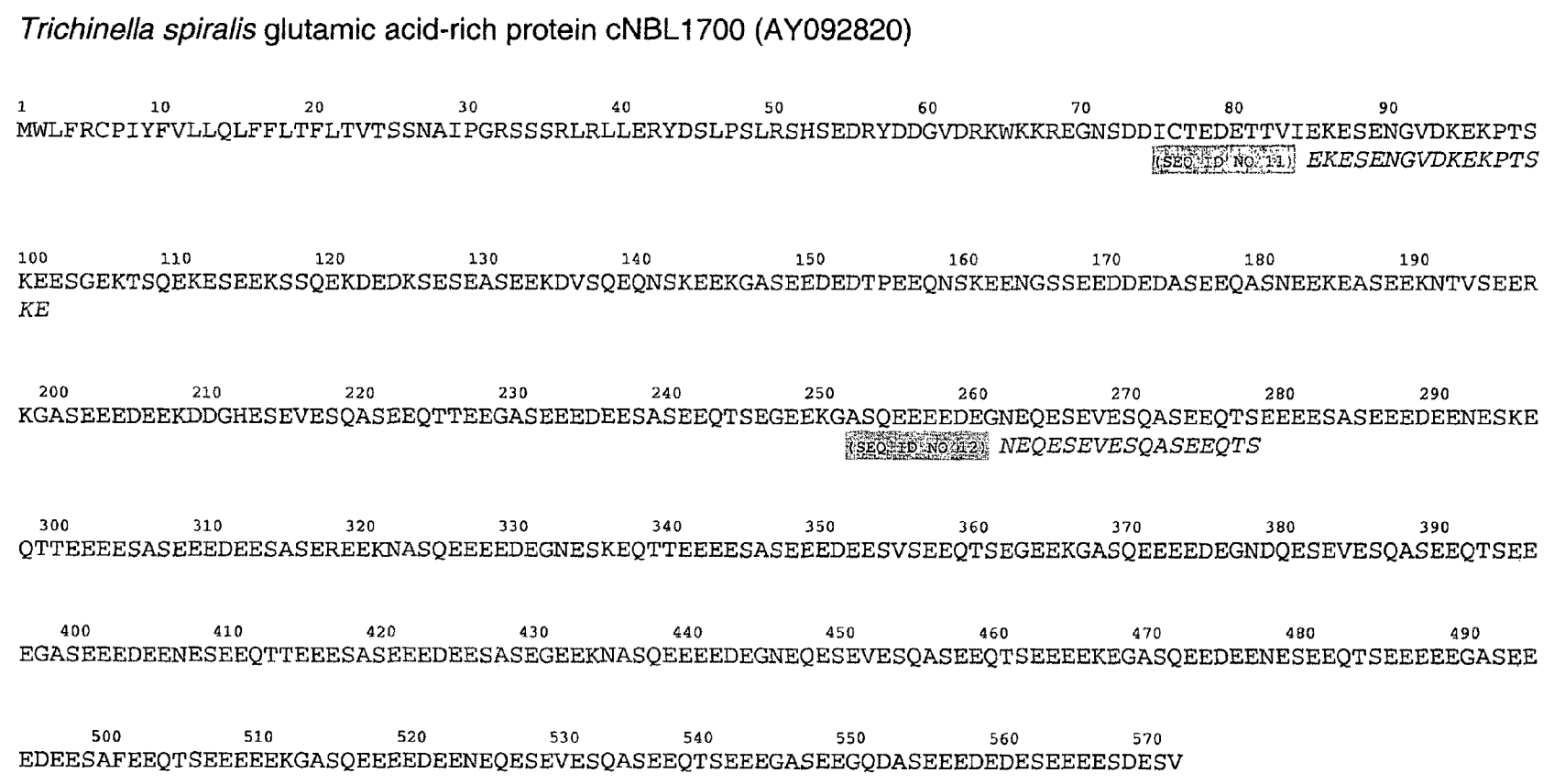

*Trichinella spiralis* glutamic acid-rich protein cNBL1700 (AY092820)

```
1        10        20        30        40        50        60        70        80        90
MWLFRCPIYFVLLQLFFLTFLTVTSSNAIPGRSSSRLRLLERYDSLPSLRSHSEDRYDDGVDRKWKKREGNSDDICTEDETTVIEKESENGVDKEKPTS
                                                                           (SEQ ID NO: 11) EKESENGVDKEKPTS 100       110       120       130       140       150       160       170       180       190
KEESGEKTSQEKESEEKSSQEKDEDKSESEASEEKDVSQEQNSKEEKGASEEDEDTPEEQNSKEENGSSEEDDEDASEEQASNEEKEASEEKNTVSEER
KE 200       210       220       230       240       250       260       270       280       290
KGASEEEDEEKDDGHESEVESQASEEQTTEEGASEEEDEESASEEQTSEGEEKGASQEEEEDEGNEQESEVESQASEEQTSEEEESASEEEDEENESKE
                                                       (SEQ ID NO: 12) NEQESEVESQASEEQTS 300       310       320       330       340       350       360       370       380       390
QTTEEEESASEEEDEESASEREEKNASQEEEEDEGNESKEQTTEEEESASEEEDEESVSEEQTSEGEEKGASQEEEEDEGNDQESEVESQASEEQTSEE 400       410       420       430       440       450       460       470       480       490
EGASEEEDEENESEEQTTEEESASEEEDEESASEGEEKNASQEEEEDEGNEQESEVESQASEEQTSEEEEKEGASQEEDEENESEEQTSEEEEEGASEE 500       510       520       530       540       550       560       570
EDEESAFEEQTSEEEEEKGASQEEEEDEENEQESEVESQASEEQTSEEEGASEEGQDASEEEDEDESEEEESDESV
```

Fig. 3

*Trichinella spiralis* 43 kDa secreted glycoprotein (M95499)

```
1        10        20        30        40        50        60        70        80        90
MRIYIFLSAFWVILHNCLQIHAANCTCRTATDDTEWFLLFKPVGLLKAKIISPANAGWANDGANMNTDSGHALVQTLAEWMGPILDDMTALGYSNTPPK
                        (SEQ ID NO:14) FLLFKPVGLLKAKIISPANAG 100       110       120       130       140       150       160       170       180       190
STITSQTTSSKGILMFGNETTDGFWLLHTFERAFPNSVAWSWPSKFTSEGHMALCLSISEDNVPLIVPALQYQEVVIYFGQVSSEKATEFADLTSLIDG
                                                                          (SEQ ID NO:15) SEKATEFADLTSLIDG 200       210       220       230       240       250       260       270       280       290
SLPTITPPLWNQQTITTLNSALSTVVYSKTSSSRLEMYGSFLAKVMVVNMRIWAVTDNTLQTTCGGKIGFVKVVKSPVTIDGTQNDRSKDKSQWAVIDD
SLP           (SEQ ID NO:16) VVYSKTSSSRLEMYGSF                                  (SEQ ID NO:17) TIDGTQNDRSKDKSQWA 300       310       320       330       340
KPVFCFTTNGYSTKQRTVAGSATCITQQVVSNLFATSAANFIPCPYS
```

Fig. 4

Trichinella spiralis 53kDa excretory/secretory antigen (U25127)

```
    1          10         20         30         40         50         60         70         80         90
    MFSITLNLFIIAFVNFQLCTCSTDNENVAMKEMTFSVPISVLQNERQFDENKLKKLLKPLGKLYKTPSDKGIPISRTEATLSVEKMVELNRLIQKEYS
                                         (SEQ ID NO: 19)
                                          QNERQFDENKLKKLLKPLGKLYKTPSD
                                          (SEQ ID NO: 20)
                                          QNERQFDENKLKKLLKPLG 100         110        120        130        140        150        160        170        180        190
    FLYKQYQKLKTVQQAEKCDDTTNVYTVTLQNTDCESKPIIEGSPATNCSDVENKHPLSCSILSKVASAEEKIIGAYCSVHLEESFPKKKSICKLSRYPG
                                                                                           (SEQ ID NO: 21)
                                                                                            LSRYPG
                                                                                            (SEQ ID NO: 22)
                                                                                            PG 200         210        220        230        240        250        260        270        280        290
    EEKFKTFVPEDVSSWFHDAIVYVPTGNRPQSNSKHSNNYRGRQGIAGLGMLPHLGAVQMNVVTIFRKNGKTTEVLSLINANDSIEIPKVFVTNPIQKPF
    EEKFKTFVPEDVS        NNYRGRQGIAGLGML                   VVTIFRKNGKTTEVLSL                          KPF
    EEKFKTFV              (SEQ ID NO: 23)                  (SEQ ID NO: 24)                    (SEQ ID NO: 26)
                                                            TIFRKNGKTTEVL
                                                           (SEQ ID NO: 25)

300         310        320        330        340        350        360        370        380        390
    GDEIDRILRKAFDTMELSNSDKEDKLQKLYNATISTKVKHRATPYDTDDAYVITEVAGVFDENKEHIGSIDKFPSDGNLQIGWKEADKSALRLKRFAKP
    GDEIDRILRKAF                                                                  KEADKSALRLKRFAKP
                                                                                  (SEQ ID NO: 27)
                                                                                       ALRLKRFAK
                                                                                       (SEQ ID NO: 28)

400         410
    PKGFFQHVFSELQLLF
    PKGFF
```

Fig. 5

*Trichinella pseudospiralis* 21 kDa excretory/secretory protein (AF269089)

```
1        10        20        30        40        50        60        70        80        90
QNMHCQYILSLLLLSLNVVFFAAGDSLDSVDDKSRRCTDEQTEVCAKTECKAEDAAMTELLLEGESDITEHPDFVYYTRCMQRCCAKLNGAKVAPLKEE 100      110       120       130       140       150       160       170
EKRRGPTKLPFQSIFDVADQQTVERCDATMCKSQRMKYESLVARTTSYKKLRASQELRDYKECIESCDAKLNGRQ
                  (SEQ ID NO:30) KSQRMKYESLVARTTSYKKLR
```

Fig. 6

*Trichinella pseudospiralis* 28 kDa excretory/secretory protein (AF348087)

```
         10         20         30         40         50         60         70         80         90
MVHFKVMNINITLLFAIILLQFISNASTERFRKLKKESMPAAVKEHLKKLMKNSIVQQSGHESEGGIVEETKQVLQKSHDSFYHLEGTIHKLEEKLEKE 110        120        130        140        150        160        170        180        190
KKLYDPWDKKDNSAKRLALGFFVRVAKQYREGLLNESGMMAGIRQPRKKCFVKYSMLDEYSATTEEDDKILMKIERKFYKCESQCQSNTKMKDFYTKDL 210        220        230        240
CILKCFEKKLDKFAEKLGVPFFDEAKVNEGVNQLQDLDKSVVPFFTSI
EKKLDKFAEKLGVPFFDEAKVN (SEQ ID NO: 32)
```

Fig. 7

SEQUENCE LISTING

```
<160> NUMBER OF SEQ ID NOS: 37

<210> SEQ ID NO 1
<211> LENGTH: 338
<212> TYPE: PRT
<213> ORGANISM: Trichinella spiralis

<400> SEQUENCE: 1

Met Phe Ile Ser Ile Ile Val Ile Leu Ile Ser Leu Lys Thr Cys Ile
1               5                   10                  15

Ala Gln Val Ala Thr Cys Lys Asn Asp Asn Asp Ala Asn Val Asp Trp
            20                  25                  30

Tyr Phe Val Tyr Lys Pro Pro Asn Val Leu Ser Ser Lys Ile Leu Gln
        35                  40                  45

Ser Gly Val Asn Pro Ala Trp Ala Ala Ser Arg Ala Asn Ile Asn Gln
    50                  55                  60

Gly Ala Gly His Ser Ile Ile Arg Thr Met Ala Ser Phe Val Val His
65                  70                  75                  80

His Ala Gln Ile Asn Val Leu Ala Tyr Ser Asp Asp Pro Pro Asn Leu
                85                  90                  95

Pro Pro Arg Asn Glu Lys Ser Lys Thr Lys Gly Val Leu Leu Val Asn
            100                 105                 110

Asn Ala Ala Asp Glu Ala Ala Trp Phe Val His Thr Val Pro Asn Phe
        115                 120                 125

Leu Ala Tyr Leu Asn Ala Tyr Ser Trp Pro Pro Ala Glu Thr Pro Lys
    130                 135                 140

Gly His Met Phe Leu Cys Val Ser Phe Asn Lys Ala His Leu Asn Ser
145                 150                 155                 160

Val Gly Lys Ala Ile Arg Tyr Gln Glu Pro Tyr Val Tyr Ala Asn Asn
                165                 170                 175

Leu Pro Ala Ala Ile Leu Asn Gln Asn Met Glu Leu Phe Asn Leu Ile
            180                 185                 190

Asn Gly Ile Asp Val Arg Val Thr Ser Phe Leu Ala His Glu Thr Phe
        195                 200                 205

Ala Thr Lys Ser Val Gln Ala Val Ala Asn Ile Gln Ala Phe Gly Lys
```

|   |   |   |   |   |   |   |   |   |   |   |   |   |   |   |
|---|---|---|---|---|---|---|---|---|---|---|---|---|---|---|
|   |   |   | 210 |   |   |   | 215 |   |   |   | 220 |   |   |   |
| His | Ser | Lys | Ser | Phe | Ala | Asp | Met | Tyr | Ala | Arg | Ile | Leu | Arg | Asn | Arg |
| 225 |   |   |   | 230 |   |   |   | 235 |   |   |   | 240 |

Phe Ala Ala Ser Ile Met Val Trp Ser Pro Ala Asp Ala Arg Ser Lys
                245                 250                 255

Ser Ile Cys Lys Gly Gln His Lys Leu Gln Lys Ile Thr Ser Ile Gln
            260                 265                 270

Leu Asp Gly Val Gln Val Ser Arg Glu Ala Asp Ser Ala Lys Trp Ala
        275                 280                 285

Leu Ile Asp Gly Lys Asn Thr Val Cys Phe Thr Thr Asn Asp Tyr Thr
    290                 295                 300

Ala Thr Glu Lys Arg Thr Pro Gly Ala Ala Val Cys Leu Glu Asn Ala
305                 310                 315                 320

Gly Val Tyr Asn Ala Phe Arg Thr Ala Ala Leu Asn Val Glu Ala Cys
                325                 330                 335

Asn Asn

<210> SEQ ID NO 2
<211> LENGTH: 25
<212> TYPE: PRT
<213> ORGANISM: Trichinella spiralis

<400> SEQUENCE: 2

Gln Ile Asn Val Leu Ala Tyr Ser Asp Asp Pro Asn Leu Pro Pro
1               5                   10                  15

Arg Asn Glu Lys Ser Lys Thr Lys Gly
            20                  25

<210> SEQ ID NO 3
<211> LENGTH: 21
<212> TYPE: PRT
<213> ORGANISM: Trichinella spiralis

<400> SEQUENCE: 3

Ile Arg Tyr Gln Glu Pro Tyr Val Tyr Ala Asn Asn Leu Pro Ala Ala
1               5                   10                  15

Ile Leu Asn Gln Asn
            20

<210> SEQ ID NO 4
<211> LENGTH: 465
<212> TYPE: PRT
<213> ORGANISM: Trichinella spiralis

<400> SEQUENCE: 4

Met His Lys Ile Thr His Lys Ser Ile Val Ser Arg His Thr Phe Ala
1               5                   10                  15

Val Tyr Leu Leu Val Ser Gly Gln Lys Leu Gln Tyr Ile Tyr Ile Phe
            20                  25                  30

Ile Cys Lys Met Ile Arg Arg Leu Phe Gln Tyr Thr Ser Met Thr Phe
        35                  40                  45

Ala Trp Ile Leu Leu Phe Leu Ser Ala Ala Ser Pro Ser Leu Gly Ala
    50                  55                  60

Phe Glu Cys Gly Val Pro His Phe Lys Pro Tyr Ile Trp Lys Ser Gly
65              70                  75                  80

Arg Ile Val Gly Gly Thr Asp Val Arg Pro His Ser His Pro Trp Gln
                85                  90                  95

Ile Gln Leu Leu Lys Ser Glu Thr Gly Gly Tyr Ser Ser Leu Cys Gly

```
                    100                 105                 110
Gly Ser Leu Val His Phe Gly Lys Pro Ser Asn Gly Thr Arg Phe Val
            115                 120                 125

Leu Thr Ala Ala His Cys Ile Thr Thr Ser Asn Met Tyr Pro Arg Thr
        130                 135                 140

Ser Arg Phe Thr Val Val Thr Gly Ala His Asn Ile Lys Met His Glu
145                 150                 155                 160

Lys Glu Lys Lys Arg Ile Pro Ile Thr Ser Tyr Tyr Val Gln His Trp
                165                 170                 175

Asn Pro Val Met Thr Thr Asn Asp Ile Ala Leu Leu Arg Leu Ala Glu
            180                 185                 190

Thr Val Tyr Tyr Asn Glu Tyr Thr Arg Pro Val Cys Leu Pro Glu Pro
        195                 200                 205

Asn Glu Glu Leu Thr Pro Gly Asp Ile Cys Val Val Thr Gly Trp Gly
    210                 215                 220

Asp Thr Thr Glu Asn Gly Thr Thr Ser Asn Thr Leu Lys Gln Val Gly
225                 230                 235                 240

Val Lys Ile Met Lys Lys Gly Thr Cys Ala Asn Val Arg Ser Glu Val
                245                 250                 255

Ile Thr Phe Cys Ala Gly Ala Met Glu Gly Gly Lys Asp Ser Cys Gln
            260                 265                 270

Gly Asp Ser Gly Gly Pro Leu Ile Cys Lys Lys Asn Gly Lys Ser Val
        275                 280                 285

Gln Phe Gly Val Val Ser Tyr Gly Thr Gly Cys Ala Arg Lys Gly Tyr
    290                 295                 300

Pro Gly Val Tyr Ala Lys Val Pro Ser Tyr Val Thr Trp Leu Asn Lys
305                 310                 315                 320

Ala Ala Lys Glu Leu Glu Asn Ser Pro Glu Gly Thr Val Lys Trp Ala
                325                 330                 335

Ser Lys Glu Asp Ser Pro Val Asp Leu Ser Thr Ala Ser Arg Pro Thr
            340                 345                 350

Asn Pro Tyr Thr Gly Ser Arg Pro Thr Ser Pro Ser Ser Gly Ser Arg
        355                 360                 365

Pro Thr Tyr Pro Ser Ser Gly Ser Arg Pro Thr Ser Pro Ser Ser Gly
    370                 375                 380

Ser Arg Pro Thr Tyr Pro Ser Ser Gly Ser Arg Pro Thr Tyr Pro Ser
385                 390                 395                 400

Ser Gly Ser Arg Pro Thr Tyr Pro Tyr Thr Gly Ser Arg Pro Thr Pro
                405                 410                 415

Gln Lys Pro Val Phe Pro Ser Tyr Gln Lys Tyr Pro Pro Ala Val Gln
            420                 425                 430

Lys Tyr Ile Asp Ser Leu Pro Ser Gly Thr Gln Gly Thr Leu Glu Tyr
        435                 440                 445

Thr Val Thr Gln Asn Gly Val Thr Thr Thr Thr Tyr Tyr His Phe Ser
    450                 455                 460

Lys
465

<210> SEQ ID NO 5
<211> LENGTH: 25
<212> TYPE: PRT
<213> ORGANISM: Trichinella spiralis

<400> SEQUENCE: 5

Met His Lys Ile Thr His Lys Ser Ile Val Ser Arg His Thr Phe Ala
```

```
                1               5                  10                 15
Val Tyr Leu Leu Val Ser Gly Gln Lys
                    20                  25

<210> SEQ ID NO 6
<211> LENGTH: 23
<212> TYPE: PRT
<213> ORGANISM: Trichinella spiralis

<400> SEQUENCE: 6

Val Gly Gly Thr Asp Val Arg Pro His Ser His Pro Trp Gln Ile Gln
1               5                   10                  15

Leu Leu Lys Ser Glu Thr Gly
            20

<210> SEQ ID NO 7
<211> LENGTH: 25
<212> TYPE: PRT
<213> ORGANISM: Trichinella spiralis

<400> SEQUENCE: 7

Leu Ser Thr Ala Ser Arg Pro Thr Asn Pro Tyr Thr Gly Ser Arg Pro
1               5                   10                  15

Thr Ser Pro Ser Ser Gly Ser Arg Pro
            20                  25

<210> SEQ ID NO 8
<211> LENGTH: 25
<212> TYPE: PRT
<213> ORGANISM: Trichinella spiralis

<400> SEQUENCE: 8

Pro Thr Tyr Pro Ser Ser Gly Ser Arg Pro Thr Tyr Pro Ser Ser Gly
1               5                   10                  15

Ser Arg Pro Thr Tyr Pro Tyr Thr Gly
            20                  25

<210> SEQ ID NO 9
<211> LENGTH: 19
<212> TYPE: PRT
<213> ORGANISM: Trichinella spiralis

<400> SEQUENCE: 9

Pro Thr Tyr Pro Ser Ser Gly Ser Arg Pro Thr Tyr Pro Ser Ser Gly
1               5                   10                  15

Ser Arg Pro

<210> SEQ ID NO 10
<211> LENGTH: 571
<212> TYPE: PRT
<213> ORGANISM: Trichinella spiralis

<400> SEQUENCE: 10

Met Trp Leu Phe Arg Cys Pro Ile Tyr Phe Val Leu Leu Gln Leu Phe
1               5                   10                  15

Phe Leu Thr Phe Leu Thr Val Thr Ser Ser Asn Ala Ile Pro Gly Arg
            20                  25                  30

Ser Ser Ser Arg Leu Arg Leu Leu Glu Arg Tyr Asp Ser Leu Pro Ser
        35                  40                  45

Leu Arg Ser His Ser Glu Asp Arg Tyr Asp Asp Gly Val Asp Arg Lys
    50                  55                  60
```

-continued

```
Trp Lys Lys Arg Glu Gly Asn Ser Asp Asp Ile Cys Thr Glu Asp Glu
 65                  70                  75                  80

Thr Thr Val Ile Glu Lys Glu Ser Glu Asn Gly Val Asp Lys Glu Lys
                 85                  90                  95

Pro Thr Ser Lys Glu Glu Ser Gly Glu Lys Thr Ser Gln Glu Lys Glu
            100                 105                 110

Ser Glu Glu Lys Ser Ser Gln Glu Lys Asp Glu Asp Lys Ser Glu Ser
        115                 120                 125

Glu Ala Ser Glu Glu Lys Asp Val Ser Gln Glu Gln Asn Ser Lys Glu
    130                 135                 140

Glu Lys Gly Ala Ser Glu Asp Glu Asp Thr Pro Glu Glu Gln Asn
145                 150                 155                 160

Ser Lys Glu Glu Asn Gly Ser Ser Glu Glu Asp Asp Glu Asp Ala Ser
                165                 170                 175

Glu Glu Gln Ala Ser Asn Glu Glu Lys Glu Ala Ser Glu Glu Lys Asn
            180                 185                 190

Thr Val Ser Glu Glu Arg Lys Gly Ala Ser Glu Glu Glu Asp Glu Glu
        195                 200                 205

Lys Asp Asp Gly His Glu Ser Glu Val Glu Ser Gln Ala Ser Glu Glu
    210                 215                 220

Gln Thr Thr Glu Glu Gly Ala Ser Glu Glu Asp Glu Glu Ser Ala
225                 230                 235                 240

Ser Glu Glu Gln Thr Ser Gly Glu Glu Lys Gly Ala Ser Gln Glu
                245                 250                 255

Glu Glu Glu Asp Glu Gly Asn Gln Glu Ser Glu Val Glu Ser Gln
            260                 265                 270

Ala Ser Glu Glu Gln Thr Ser Glu Glu Glu Ser Ala Ser Glu Glu
        275                 280                 285

Glu Asp Glu Glu Asn Glu Ser Lys Glu Gln Thr Thr Glu Glu Glu
    290                 295                 300

Ser Ala Ser Glu Glu Asp Glu Glu Ser Ala Ser Glu Arg Glu Glu
305                 310                 315                 320

Lys Asn Ala Ser Gln Glu Glu Glu Asp Glu Gly Asn Glu Ser Lys
                325                 330                 335

Glu Gln Thr Thr Glu Glu Glu Ser Ala Ser Glu Glu Glu Asp Glu
            340                 345                 350

Glu Ser Val Ser Glu Glu Gln Thr Ser Glu Gly Glu Glu Lys Gly Ala
        355                 360                 365

Ser Gln Glu Glu Glu Glu Asp Glu Gly Asn Asp Gln Glu Ser Glu Val
    370                 375                 380

Glu Ser Gln Ala Ser Glu Glu Gln Thr Ser Glu Glu Glu Gly Ala Ser
385                 390                 395                 400

Glu Glu Glu Asp Glu Glu Asn Glu Ser Glu Glu Gln Thr Thr Glu Glu
                405                 410                 415

Glu Ser Ala Ser Glu Glu Glu Asp Glu Glu Ser Ala Ser Glu Gly Glu
            420                 425                 430

Glu Lys Asn Ala Ser Gln Glu Glu Glu Asp Glu Gly Asn Glu Gln
        435                 440                 445

Glu Ser Glu Val Glu Ser Gln Ala Ser Glu Glu Gln Thr Ser Glu Glu
    450                 455                 460

Glu Glu Lys Glu Gly Ala Ser Gln Glu Glu Asp Glu Glu Asn Glu Ser
465                 470                 475                 480

Glu Glu Gln Thr Ser Glu Glu Glu Glu Glu Gly Ala Ser Glu Glu Glu
                485                 490                 495
```

Asp Glu Glu Ser Ala Phe Glu Glu Gln Thr Ser Glu Glu Glu Glu
                500                 505                 510

Lys Gly Ala Ser Gln Glu Glu Glu Asp Glu Glu Asn Glu Gln Glu
        515                 520                 525

Ser Glu Val Glu Ser Gln Ala Ser Glu Glu Gln Thr Ser Glu Glu Glu
        530                 535                 540

Gly Ala Ser Glu Glu Gly Gln Asp Ala Ser Glu Glu Glu Asp Glu Asp
545                 550                 555                 560

Glu Ser Glu Glu Glu Glu Ser Asp Glu Ser Val
                565                 570

<210> SEQ ID NO 11
<211> LENGTH: 17
<212> TYPE: PRT
<213> ORGANISM: Trichinella spiralis

<400> SEQUENCE: 11

Glu Lys Glu Ser Glu Asn Gly Val Asp Lys Glu Lys Pro Thr Ser Lys
1               5                   10                  15
Glu

<210> SEQ ID NO 12
<211> LENGTH: 17
<212> TYPE: PRT
<213> ORGANISM: Trichinella spiralis

<400> SEQUENCE: 12

Asn Glu Gln Glu Ser Glu Val Glu Ser Gln Ala Ser Glu Glu Gln Thr
1               5                   10                  15
Ser

<210> SEQ ID NO 13
<211> LENGTH: 347
<212> TYPE: PRT
<213> ORGANISM: Trichinella spiralis

<400> SEQUENCE: 13

Met Arg Ile Tyr Ile Phe Leu Ser Ala Phe Trp Val Ile Leu His Asn
1               5                   10                  15

Cys Leu Gln Ile His Ala Ala Asn Cys Thr Cys Arg Thr Ala Thr Asp
                20                  25                  30

Asp Thr Glu Trp Phe Leu Leu Phe Lys Pro Val Gly Leu Leu Lys Ala
            35                  40                  45

Lys Ile Ile Ser Pro Ala Asn Ala Gly Trp Ala Asn Asp Gly Ala Asn
        50                  55                  60

Met Asn Thr Asp Ser Gly His Ala Leu Val Gln Thr Leu Ala Glu Trp
65                  70                  75                  80

Met Gly Pro Ile Leu Asp Asp Met Thr Ala Leu Gly Tyr Ser Asn Thr
                85                  90                  95

Pro Pro Lys Ser Thr Ile Thr Ser Gln Thr Thr Ser Ser Lys Gly Ile
            100                 105                 110

Leu Met Phe Gly Asn Glu Thr Thr Asp Gly Phe Trp Leu Leu His Thr
        115                 120                 125

Phe Glu Arg Ala Phe Pro Asn Ser Val Ala Trp Ser Trp Pro Ser Lys
    130                 135                 140

Phe Thr Ser Glu Gly His Met Ala Leu Cys Leu Ser Ile Ser Glu Asp
145                 150                 155                 160

```
        Asn Val Pro Leu Ile Val Pro Ala Leu Gln Tyr Gln Glu Val Val Ile
                        165                 170                 175

Tyr Phe Gly Gln Val Ser Ser Glu Lys Ala Thr Glu Phe Ala Asp Leu
                    180                 185                 190

Thr Ser Leu Ile Asp Gly Ser Leu Pro Thr Ile Thr Pro Pro Leu Trp
                195                 200                 205

Asn Gln Gln Thr Ile Thr Thr Leu Asn Ser Ala Leu Ser Thr Val Val
            210                 215                 220

Tyr Ser Lys Thr Ser Ser Ser Arg Leu Glu Met Tyr Gly Ser Phe Leu
        225                 230                 235                 240

Ala Lys Val Met Val Val Asn Met Arg Ile Trp Ala Val Thr Asp Asn
                        245                 250                 255

Thr Leu Gln Thr Thr Cys Gly Gly Lys Ile Gly Phe Val Lys Val Val
                    260                 265                 270

Lys Ser Pro Val Thr Ile Asp Gly Thr Gln Asn Asp Arg Ser Lys Asp
                275                 280                 285

Lys Ser Gln Trp Ala Val Ile Asp Asp Ser Leu Pro Lys Pro Val Phe
            290                 295                 300

Cys Phe Thr Thr Asn Gly Tyr Ser Thr Lys Gln Arg Thr Val Ala Gly
        305                 310                 315                 320

Ser Ala Thr Cys Ile Thr Gln Gln Val Val Ser Asn Leu Phe Ala Thr
                        325                 330                 335

Ser Ala Ala Asn Phe Ile Pro Cys Pro Tyr Ser
                    340                 345

<210> SEQ ID NO 14
<211> LENGTH: 21
<212> TYPE: PRT
<213> ORGANISM: Trichinella spiralis

<400> SEQUENCE: 14

Phe Leu Leu Phe Lys Pro Val Gly Leu Leu Lys Ala Lys Ile Ile Ser
1               5                   10                  15

Pro Ala Asn Ala Gly
            20

<210> SEQ ID NO 15
<211> LENGTH: 19
<212> TYPE: PRT
<213> ORGANISM: Trichinella spiralis

<400> SEQUENCE: 15

Ser Glu Lys Ala Thr Glu Phe Ala Asp Leu Thr Ser Leu Ile Asp Gly
1               5                   10                  15

Ser Leu Pro

<210> SEQ ID NO 16
<211> LENGTH: 17
<212> TYPE: PRT
<213> ORGANISM: Trichinella spiralis

<400> SEQUENCE: 16

Val Val Tyr Ser Lys Thr Ser Ser Ser Arg Leu Glu Met Tyr Gly Ser
1               5                   10                  15

Phe

<210> SEQ ID NO 17
<211> LENGTH: 17
<212> TYPE: PRT
```

<213> ORGANISM: Trichinella spiralis

<400> SEQUENCE: 17

Thr Ile Asp Gly Thr Gln Asn Asp Arg Ser Lys Asp Lys Ser Gln Trp
1               5                   10                  15

Ala

<210> SEQ ID NO 18
<211> LENGTH: 412
<212> TYPE: PRT
<213> ORGANISM: Trichinella spiralis

<400> SEQUENCE: 18

Met Phe Ser Ile Thr Leu Asn Leu Phe Ile Ile Ala Phe Val Asn Phe
1               5                   10                  15

Gln Leu Cys Thr Cys Ser Thr Asp Asn Glu Asn Val Ala Met Lys Glu
            20                  25                  30

Met Thr Phe Ser Val Pro Ile Ser Val Leu Gln Asn Glu Arg Gln Phe
        35                  40                  45

Asp Glu Asn Lys Leu Lys Lys Leu Leu Lys Pro Leu Gly Lys Leu Tyr
    50                  55                  60

Lys Thr Pro Ser Asp Lys Gly Ile Pro Ile Ser Arg Thr Glu Ala Thr
65                  70                  75                  80

Leu Ser Val Glu Lys Met Met Val Glu Leu Asn Arg Leu Ile Gln Lys
                85                  90                  95

Glu Tyr Ser Phe Leu Tyr Lys Gln Tyr Gln Lys Leu Lys Thr Val Gln
            100                 105                 110

Gln Ala Glu Lys Cys Asp Asp Thr Thr Asn Val Tyr Thr Val Thr Leu
        115                 120                 125

Gln Asn Thr Asp Cys Glu Ser Lys Pro Ile Ile Glu Gly Ser Pro Ala
    130                 135                 140

Thr Asn Cys Ser Asp Val Glu Asn Lys His Pro Leu Ser Cys Ser Ile
145                 150                 155                 160

Leu Ser Lys Val Ala Ser Ala Glu Glu Lys Ile Ile Gly Ala Tyr Cys
                165                 170                 175

Ser Val His Leu Glu Glu Ser Phe Pro Lys Lys Ser Ile Cys Lys
            180                 185                 190

Leu Ser Arg Tyr Pro Gly Glu Glu Lys Phe Lys Thr Phe Val Pro Glu
        195                 200                 205

Asp Val Ser Ser Trp Phe His Asp Ala Ile Val Tyr Val Pro Thr Gly
    210                 215                 220

Asn Arg Pro Gln Ser Asn Ser Lys His Ser Asn Asn Tyr Arg Gly Arg
225                 230                 235                 240

Gln Gly Ile Ala Gly Leu Gly Met Leu Pro His Leu Gly Ala Val Gln
                245                 250                 255

Met Asn Val Val Thr Ile Phe Arg Lys Asn Gly Lys Thr Thr Glu Val
            260                 265                 270

Leu Ser Leu Ile Asn Ala Asn Asp Ser Ile Glu Ile Pro Lys Val Phe
        275                 280                 285

Val Thr Asn Pro Ile Gln Lys Pro Phe Gly Asp Glu Ile Asp Arg Ile
    290                 295                 300

Leu Arg Lys Ala Phe Asp Thr Met Glu Leu Ser Asn Ser Asp Lys Glu
305                 310                 315                 320

Asp Lys Leu Gln Lys Leu Tyr Asn Ala Thr Ile Ser Thr Lys Val Lys
                325                 330                 335

```
His Arg Ala Thr Pro Tyr Asp Thr Asp Asp Ala Tyr Val Ile Thr Glu
            340                 345                 350

Val Ala Gly Val Phe Asp Glu Asn Lys Glu His Ile Gly Ser Ile Asp
        355                 360                 365

Lys Phe Pro Ser Asp Gly Asn Leu Gln Ile Gly Trp Lys Glu Ala Asp
370                 375                 380

Lys Ser Ala Leu Arg Leu Lys Arg Phe Ala Lys Pro Pro Lys Gly Phe
385                 390                 395                 400

Phe Gln His Val Phe Ser Glu Leu Gln Leu Leu Phe
                405                 410
```

<210> SEQ ID NO 19
<211> LENGTH: 27
<212> TYPE: PRT
<213> ORGANISM: Trichinella spiralis

<400> SEQUENCE: 19

```
Gln Asn Glu Arg Gln Phe Asp Glu Asn Lys Leu Lys Lys Leu Leu Lys
1               5                   10                  15

Pro Leu Gly Lys Leu Tyr Lys Thr Pro Ser Asp
            20                  25
```

<210> SEQ ID NO 20
<211> LENGTH: 19
<212> TYPE: PRT
<213> ORGANISM: Trichinella spiralis

<400> SEQUENCE: 20

```
Gln Asn Glu Arg Gln Phe Asp Glu Asn Lys Leu Lys Lys Leu Leu Lys
1               5                   10                  15

Pro Leu Gly
```

<210> SEQ ID NO 21
<211> LENGTH: 19
<212> TYPE: PRT
<213> ORGANISM: Trichinella spiralis

<400> SEQUENCE: 21

```
Leu Ser Arg Tyr Pro Gly Glu Glu Lys Phe Lys Thr Phe Val Pro Glu
1               5                   10                  15

Asp Val Ser
```

<210> SEQ ID NO 22
<211> LENGTH: 11
<212> TYPE: PRT
<213> ORGANISM: Trichinella spiralis

<400> SEQUENCE: 22

```
Pro Gly Glu Glu Lys Phe Lys Thr Phe Val Pro
1               5                   10
```

<210> SEQ ID NO 23
<211> LENGTH: 15
<212> TYPE: PRT
<213> ORGANISM: Trichinella spiralis

<400> SEQUENCE: 23

```
Asn Asn Tyr Arg Gly Arg Gln Gly Ile Ala Gly Leu Gly Met Leu
1               5                   10                  15
```

<210> SEQ ID NO 24
<211> LENGTH: 17

```
<212> TYPE: PRT
<213> ORGANISM: Trichinella spiralis

<400> SEQUENCE: 24

Val Val Thr Ile Phe Arg Lys Asn Gly Lys Thr Thr Glu Val Leu Ser
1               5                   10                  15

Leu

<210> SEQ ID NO 25
<211> LENGTH: 13
<212> TYPE: PRT
<213> ORGANISM: Trichinella spiralis

<400> SEQUENCE: 25

Thr Ile Phe Arg Lys Asn Gly Lys Thr Thr Glu Val Leu
1               5                   10

<210> SEQ ID NO 26
<211> LENGTH: 15
<212> TYPE: PRT
<213> ORGANISM: Trichinella spiralis

<400> SEQUENCE: 26

Lys Pro Phe Gly Asp Glu Ile Asp Arg Ile Leu Arg Lys Ala Phe
1               5                   10                  15

<210> SEQ ID NO 27
<211> LENGTH: 21
<212> TYPE: PRT
<213> ORGANISM: Trichinella spiralis

<400> SEQUENCE: 27

Lys Glu Ala Asp Lys Ser Ala Leu Arg Leu Lys Arg Phe Ala Lys Pro
1               5                   10                  15

Pro Lys Gly Phe Phe
            20

<210> SEQ ID NO 28
<211> LENGTH: 9
<212> TYPE: PRT
<213> ORGANISM: Trichinella spiralis

<400> SEQUENCE: 28

Ala Leu Arg Leu Lys Arg Phe Ala Lys
1               5

<210> SEQ ID NO 29
<211> LENGTH: 174
<212> TYPE: PRT
<213> ORGANISM: Trichinella pseudospiralis

<400> SEQUENCE: 29

Gln Asn Met His Cys Gln Tyr Ile Leu Ser Leu Leu Leu Ser Leu
1               5                   10                  15

Asn Val Val Phe Phe Ala Ala Gly Asp Ser Leu Asp Ser Val Asp Asp
                20                  25                  30

Lys Ser Arg Arg Cys Thr Asp Glu Gln Thr Glu Val Cys Ala Lys Thr
            35                  40                  45

Glu Cys Lys Ala Glu Asp Ala Ala Met Thr Glu Leu Leu Leu Glu Gly
        50                  55                  60

Glu Ser Asp Ile Thr Glu His Pro Asp Phe Val Tyr Tyr Thr Arg Cys
65                  70                  75                  80
```

```
Met Gln Arg Cys Cys Ala Lys Leu Asn Gly Ala Lys Val Ala Pro Leu
                85                  90                  95

Lys Glu Glu Glu Lys Arg Arg Gly Pro Thr Lys Leu Pro Phe Gln Ser
            100                 105                 110

Ile Phe Asp Val Ala Asp Gln Gln Thr Val Glu Arg Cys Asp Ala Thr
            115                 120                 125

Met Cys Lys Ser Gln Arg Met Lys Tyr Glu Ser Leu Val Ala Arg Thr
        130                 135                 140

Thr Ser Tyr Lys Lys Leu Arg Ala Ser Gln Glu Leu Arg Asp Tyr Lys
145                 150                 155                 160

Glu Cys Ile Glu Ser Cys Asp Ala Lys Leu Asn Gly Arg Gln
                165                 170
```

<210> SEQ ID NO 30
<211> LENGTH: 21
<212> TYPE: PRT
<213> ORGANISM: Trichinella pseudospiralis

<400> SEQUENCE: 30

```
Lys Ser Gln Arg Met Lys Tyr Glu Ser Leu Val Ala Arg Thr Thr Ser
1               5                   10                  15

Tyr Lys Lys Leu Arg
            20
```

<210> SEQ ID NO 31
<211> LENGTH: 244
<212> TYPE: PRT
<213> ORGANISM: Trichinella pseudospiralis

<400> SEQUENCE: 31

```
Met Val His Phe Lys Val Met Asn Ile Asn Ile Thr Leu Leu Phe Ala
1               5                   10                  15

Ile Ile Leu Leu Gln Phe Ile Ser Asn Ala Ser Thr Glu Arg Phe Arg
                20                  25                  30

Lys Leu Lys Lys Glu Ser Met Pro Ala Ala Val Lys Glu His Leu Lys
            35                  40                  45

Lys Leu Met Lys Asn Ser Ile Val Gln Gln Ser Gly His Glu Ser Glu
        50                  55                  60

Gly Gly Ile Val Glu Glu Thr Lys Gln Val Leu Gln Lys Ser His Asp
65                  70                  75                  80

Ser Phe Tyr His Leu Glu Gly Thr Ile His Lys Leu Glu Glu Lys Leu
                85                  90                  95

Glu Lys Glu Lys Lys Leu Tyr Asp Pro Trp Asp Lys Lys Asp Asn Ser
            100                 105                 110

Ala Lys Arg Leu Ala Leu Gly Phe Phe Val Arg Val Ala Lys Gln Tyr
        115                 120                 125

Arg Glu Gly Leu Leu Asn Glu Ser Gly Met Met Ala Gly Ile Arg Gln
    130                 135                 140

Pro Arg Lys Lys Cys Phe Val Lys Tyr Ser Met Leu Asp Glu Tyr Ser
145                 150                 155                 160

Ala Thr Thr Glu Glu Asp Asp Lys Ile Leu Met Lys Ile Glu Arg Lys
                165                 170                 175

Phe Tyr Lys Cys Glu Ser Gln Cys Gln Ser Thr Lys Met Lys Asp
            180                 185                 190

Phe Tyr Thr Lys Asp Leu Cys Ile Leu Lys Cys Phe Glu Lys Lys Leu
        195                 200                 205

Asp Lys Phe Ala Glu Lys Leu Gly Val Pro Phe Asp Glu Ala Lys Val
```

```
              210                 215                 220
Asn Glu Gly Val Asn Gln Leu Gln Asp Leu Asp Lys Ser Val Val Pro
            225                 230                 235                 240

Phe Thr Ser Ile

<210> SEQ ID NO 32
<211> LENGTH: 21
<212> TYPE: PRT
<213> ORGANISM: Trichinella pseudospiralis

<400> SEQUENCE: 32

Glu Lys Lys Leu Asp Lys Phe Ala Glu Lys Leu Gly Val Pro Phe Asp
1               5                  10                  15

Glu Ala Lys Val Asn
            20

<210> SEQ ID NO 33
<211> LENGTH: 8
<212> TYPE: PRT
<213> ORGANISM: Artificial sequence
<220> FEATURE:
<223> OTHER INFORMATION: Linker peptide

<400> SEQUENCE: 33

Asp Tyr Lys Asp Asp Asp Asp Lys
1               5

<210> SEQ ID NO 34
<211> LENGTH: 17
<212> TYPE: PRT
<213> ORGANISM: Artificial sequence
<220> FEATURE:
<223> OTHER INFORMATION: Linker peptide

<400> SEQUENCE: 34

Gly Gly Gly Gly Gly Gly Gly Gly Asp Tyr Lys Asp Asp Asp
1               5                  10                  15

Lys

<210> SEQ ID NO 35
<211> LENGTH: 18
<212> TYPE: PRT
<213> ORGANISM: Artificial sequence
<220> FEATURE:
<223> OTHER INFORMATION: Linker peptide

<400> SEQUENCE: 35

Pro Gly Gly Gly Gly Gly Gly Gly Gly Asp Tyr Lys Asp Asp Asp
1               5                  10                  15

Asp Lys

<210> SEQ ID NO 36
<211> LENGTH: 18
<212> TYPE: PRT
<213> ORGANISM: Artificial sequence
<220> FEATURE:
<223> OTHER INFORMATION: Linker peptide

<400> SEQUENCE: 36

Trp Gly Gly Gly Gly Gly Gly Gly Gly Asp Tyr Lys Asp Asp Asp
1               5                  10                  15

Asp Lys
```

```
<210> SEQ ID NO 37
<211> LENGTH: 19
<212> TYPE: PRT
<213> ORGANISM: Artificial sequence
<220> FEATURE:
<223> OTHER INFORMATION: Linker peptide

<400> SEQUENCE: 37

Trp Trp Gly Gly Gly Gly Gly Gly Gly Gly Asp Tyr Lys Asp Asp
1               5                   10                  15

Asp Asp Lys
```

DIAGNOSTIC COMPOSITION AND METHOD FOR THE DETECTION OF A *TRICHINELLA* INFECTION

BACKGROUND OF INVENTION

1. Field of Invention

The present invention relates to a diagnostic composition and method for the detection of an infection by the nematode *Trichinella* spp in a body fluid sample from animals or humans, preferably in serum or meat juice of pigs or other susceptible organisms and to diagnostic kits that can be used for monitoring and surveillance for *Trichinella* infections or for testing of individual carcasses for food safety.

2. Description of Related Art

*Trichinella* spp. is a group of nematodes that can occur worldwide. There are eight different species; the species of main importance in Europe are *Trichinella spiralis*, *Trichinella britovi*, *Trichinella pseudospiralis*, and *Trichinella nativa*. *Trichinella* spp. can infect a wide variety of species including humans, pigs, rats, bears, horses and birds.

The parasitic nematode *Trichinella* undergoes a distinct live cycle. Larvae are ingested by eating raw or undercooked meat. They are released from nurse cells in the stomach from where they enter the small intestine, where adults mature. Females shed newborn larvae that enter the lymph, reach the venous blood and settle in voluntary muscles, especially those of the diaphragm, tongue and masseters. Larvae mature and form nurse cell-larvae complexes that calcify.

*Trichinella* infection in production animals is important because of the risk for humans to contract trichinellosis following consumption of raw or undercooked meat from infected animals. Human trichinellosis is a serious disease that can cause much suffering and may result in death.

There are three different diagnostic methods to detect *Trichinella* spp. in animals.

Two methods are based on the detection of the parasite; the third method is based on the detection of antibodies against this nematode.

The first method called "Trichinoscopy" or the compressorium method is a direct detection method in which tissue is compressed between two glass plates and studied microscopically. This method is rather insensitive and labour-intense. More important, non-encapsulating *Trichinella* species such as *T. pseudospiralis* may not be detected with this method.

The second method called "digestion method" is a more sensitive direct detection method in which muscle tissue surrounding the larvae is artificially digested to release the larvae. Subsequently, the number of larvae can be determined microscopically. The detection limit by artificial digestion of 1 g tissue is 3-5 larvae per gram.

The third method is an indirect detection method using serology to detect antibodies against *Trichinella* spp. As antigens the excretory/secretory (E/S) antigens can be used. Although this method is currently not recommended for meat inspection or food safety programs, it is an important tool for surveillance programs and epidemiological investigations in animal populations. Serology can be based on blood serum or meat juice. This method has a limit of detection of 0.01 larvae per gram tissue.

For the purpose of ensuring food safety, all pig carcasses must be tested as part of the post-mortem examination. Carcasses may be cut up in a maximum of six parts, or be cut up in a cutting plant adjacent to the slaughterhouse before the results of the *Trichinella* tests are available, but further processing can only take place after the *Trichinella* tests have shown negative results.

According to EU Regulation Trichinoscopy will no longer be permitted as a standard method of examination, although it may be used as a transitional measure during a period of maximum four years following the date of application of the new EU Regulation.

The prescribed method for *Trichinella* examinations will be the digestion method with the magnetic stirrer method for pooled sample digestion. Equivalent methods are the mechanically assisted (Stomacher) pooled sample digestion method using 'sedimentation technique', the mechanically assisted (Stomacher) pooled sample digestion method using 'on filter isolation technique', and the automatic digestion method (Trichomatic 35) for pooled samples of up to 35 gram.

Currently used *Trichinella* digestion tests have a number of disadvantages.

All digestion methods are labour intensive as they require manual inspection of the filtered digestion mixture by microscopy performed by an experienced investigator. No routine training of investigators or testing of proficiency panels to assure validity of the inspection procedure is provided by current EU regulation. As a rule the investigators performing the digestion method know positive test results only from their initial training.

Finally currently approved test methods do not allow tracking of the samples and documentation of the results.

At present as stated above serological methods are considered useful for monitoring purposes but are not considered suitable for the detection of *Trichinella* infection in individual animals intended for human consumption. In most cases problems in known serological methods result from the diagnostic antigens used. The presently used crude antigens or E/S antigens include antigenic components that may react non-specifically and thus produce false positive results. Additionally the diagnostic window and selectivity of known serological tests using e.g. E/S antigens is considered to be too small. Finally, known serological methods require special technical and personal equipment which at present is not available in slaughterhouses.

When comparing both systems it appears that on principle serological tests have a number of advantages over digestion methods and that if improved they could be an interesting alternative also in routine testing.

Some of the disadvantages mentioned above can be met by using different antigens. In this context Ting-Xian et al. e.g. describe (Chin. J. Parasitol. Dis.; June 2005, No. 3; 143) the use of T668 antigen as diagnostic antigen in immunoassays. However, also here the problems regarding the narrow diagnostic window remain.

BRIEF SUMMARY OF THE INVENTION

The object of the invention is to provide compositions and methods which allow the design of improved serological tests.

The object of the invention is realised by a diagnostic composition and a method to detect antibodies in a sample obtained from an animal or human being infected by *Trichinella*. Additionally covered by the invention are kits, specific peptides, fusion peptides and tracer complexes especially for use in fluorescence polarisation.

A diagnostic composition according to the invention comprises at least one peptide containing a series of amino acids that form a continuous or discontinuous epitope recognized by sera from pigs infected with *Trichinella*.

The term "peptide" comprises native forms of peptides as well as recombinant peptides and chemically synthesized peptides. Unless explicitly mentioned the term peptide when used in this application will always denote a series of amino acids that form a continuous or discontinuous epitope recognized by sera from pigs infected with *Trichinella*.

The term "sample" shall include any material in which antibodies against *Trichinella* can be detected. Typical sample materials are body fluids like blood, serum, plasma, urine and saliva to give only some examples. Further sample materials which can be used in animal testing are meat and meat juice.

By mapping experiments a number of different peptides were identified by the applicants, which can be used either alone or in combination in the diagnostic composition or methods. Each peptide according to the invention corresponds to a part of an antigen expressed by *Trichinella*.

In the mapping experiments sera from *Trichinella* infected animals, especially pigs were used to identify different series of amino acids that form a continuous or discontinuous epitope on *Trichinella* antigens. Especially the excretory secretory antigenic proteins but also further antigens related to different stages of the infection cycle were mapped.

A number of preferred peptides which can be used with the invention and the proteins to which they belong are identified in the following:

```
Trichinella spiralis newborn larvae-specific
protein
SS1 (SEQ ID NO 1):
MFISIIVILI SLKTCIAQVA TCKNDNDANV DWYFVYKPPN

VLSSKILQSG VNPAWAASRA NINQGAGHSI IRTMASFVVH

HAQINVLAYS DDPPNLPPRN EKSKTKGVLL VNNAADEAAW

FVHTVPNFLA YLNAYSWPPA ETPKGHMFLC VSFNKAHLNS

VGKAIRYQEP YVYANNLPAA ILNQNMELFN LINGIDVRVT

SFLAHETFAT KSVQAVANIQ AFGKHSKSFA DMYARILRNR

FAASIMVWSP ADARSKSICK GQHKLQKITS IQLDGVQVSR

EADSAKWALI DGKNTVCFTT NDYTATEKRT PGAAVCLENA

GVYNAFRTAA LNVEACNN
```

Preferred peptides having an amino acid sequence of SS1 are:

```
SEQ ID NO 2:
QINVLAYSDD PPNLPPRNEK SKTKG
and

SEQ ID NO 3:
IRYQEPYVYA NNLPAAILNQ N

Trichinella spiralis newborn larvae-specific
protein
SS2 (SEQ ID NO 4):
MHKITHKSIV SRHTFAVYLL VSGQKLQYIY IFICKMIRRL

FQYTSMTFAW ILLFLSAASP SLGAFECGVP HFKPYIWKSG

RIVGGTDVRP HSHPWQIQLL KSETGGYSSL CGGSLVHFGK

PSNGTRFVLT AAHCITTSNM YPRTSRFTVV TGAHNIKMHE

KEKKRIPITS YYVQHWNPVM TTNDIALLRL AETVYYNEYT
```

```
RPVCLPEPNE ELTPGDICVV TGWGDTTENG TTSNTLKQVG

VKIMKKGTCA NVRSEVITFC AGAMEGGKDS CQGDSGGPLI

CKKNGKSVQF GVVSYGTGCA RKGYPGVYAK VPSYVTWLNK

AAKELENSPE GTVKWASKED SPVDLSTASR PTNPYTGSRP

TSPSSGSRPT YPSSGSRPTS PSSGSRPTYP SSGSRPTYPS

SGSRPTYPYT GSRPTPQKPV FPSYQKYPPA VQKYIDSLPS

GTQGTLEYTV TQNGVTTTTY YHFSK
```

Preferred peptides having an amino acid sequence of SS2 are:

```
SEQ ID NO 5:
MHKITHKSIV SRHTFAVYLL VSGQK

SEQ ID NO 6:
VGGTDVRPHSH PWQIQLLKSET G

SEQ ID NO 7:
LSTASRPTNP YTGSRPTSPS SGSRP

SEQ ID NO 8:
PTYPSSGSRP TYPSSGSRPT YPYTG
and

SEQ ID NO 9:
PTYPSSGSRP TYPSSGSRP

Trichinella spiralis glutamic acid-rich
protein
cNBL1700 (SEQ ID NO 10):
MWLFRCPIYF VLLQLFFLTF LTVTSSNAIP GRSSSRLRLL

ERYDSLPSLR SHSEDRYDDG VDRKWKKREG NSDDICTEDE

TTVIEKESEN GVDKEKPTSK EESGEKTSQE KESEEKSSQE

KDEDKSESEA SEEKDVSQEQ NSKEEKGASE EDEDTPEEQN

SKEENGSSEE DDEDASEEQA SNEEKEASEE KNTVSEERKG

ASEEEDEEKD DGHESEVESQ ASEEQTTEEG ASEEEDEESA

SEEQTSEGEE KGASQEEEED EGNEQESEVE SQASEEQTSE

EEESASEEED EENESKEQTT EEEESASEEE DEESASEREE

KNASQEEEED EGNESKEQTT EEEESASEEE DEESVSEEQT

SEGEEKGASQ EEEEDEGNDQ ESEVESQASE EQTSEEEGAS

EEEDEENESE EQTTEEESAS EEEDEESASE GEEKNASQEE

EEDEGNEQES EVESQASEEQ TSEEEEKEGA SQEEDEENES

EEQTSEEEEE GASEEEDEES AFEEQTSEEE EEKGASQEEE

EDEENEQESE VESQASEEQT SEEEGASEEG QDASEEEDED

ESEEEESDES V
```

Preferred peptides having an amino acid sequence of cNBL1700 are:

```
SEQ ID NO 11:
EKESENGVDK EKPTSKE
and

SEQ ID NO 12:
NEQESEVESQ ASEEQTS
```

*Trichinella spiralis* 43 kDa secreted
glycoprotein (SEQ ID NO 13):
MRIYIFLSAF WVILHNCLQI HAANCTCRTA TDDTEWFLLF

KPVGLLKAKI ISPANAGWAN DGANMNTDSG HALVQTLAEW

MGPILDDMTA LGYSNTPPKS TITSQTTSSK GILMFGNETT

DGFWLLHTFE RAFPNSVAWS WPSKFTSEGH MALCLSISED

NVPLIVPALQ YQEVVIYFGQ VSSEKATEFA DLTSLIDGSL

PTITPPLWNQ QTITTLNSAL STVVYSKTSS SRLEMYGSFL

AKVMVVNMRI WAVTDNTLQT TCGGKIGFVK VVKSPVTIDG

TQNDRSKDKS QWAVIDDSLP KPVFCFTTNG YSTKQRTVAG

SATCITQQVV SNLFATSAAN FIPCPYS

Preferred peptides having an amino acid sequence of 43 kDa secreted glycoprotein are:

SEQ ID NO 14:
FLLFKPVGLL KAKIISPANA G

SEQ ID NO 15:
SEKATEFADL TSLIDGSLP

SEQ ID NO 16:
VVYSKTSSSR LEMYGSF
and

SEQ ID NO 17:
TIDGTQNDRS KDKSQWA

*Trichinella spiralis* 53 kDa excretory/
secretory antigen (SEQ ID NO 18):
MFSITLNLFI IAFVNFQLCT CSTDNENVAM KEMTFSVPIS

VLQNERQFDE NKLKKLLKPL GKLYKTPSDK GIPISRTEAT

LSVEKMMVEL NRLIQKEYSF LYKQYQKLKT VQQAEKCDDT

TNVYTVTLQN TDCESKPIIE GSPATNCSDV ENKHPLSCSI

LSKVASAEEK IIGAYCSVHL EESFPKKKSI CKLSRYPGEE

KFKTFVPEDV SSWFHDAIVY VPTGNRPQSN SKHSNNYRGR

QGIAGLGMLP HLGAVQMNVV TIFRKNGKIT EVLSLINAND

SIEIPKVFVT NPIQKPFGDE IDRILRKAFD TMELSNSDKE

DKLQKLYNAT ISTKVKHRAT PYDTDDAYVI TEVAGVFDEN

KEHIGSIDKF PSDGNLQIGW KEADKSALRL KRFAKPPKGF

FQHVFSELQL LF

Preferred peptides having an amino acid sequence of 53 kDa excretory/secretory antigen are:

SEQ ID NO 19:
QNERQFDENK LKKLLKPLGK LYKTPSD

SEQ ID NO 20:
QNERQFDENK LKKLLKPLG

SEQ ID NO 21:
LSRYPGEEKF KTFVPEDVS

SEQ ID NO 22:
PGEEKFKTFV P

SEQ ID NO 23:
NNYRGRQGIA GLGML

SEQ ID NO 24:
VVTIFRKNGK TTEVLSL

SEQ ID NO 25:
TIFRKNGKTT EVL

SEQ ID NO 26:
KPFGDEIDRI LRKAF

SEQ ID NO 27:
KEADKSALRL KRFAKPPKGF F

SEQ ID NO 28:
ALRLKRFAK

*Trichinella pseudospiralis* 21 kDa excretory/
secretory protein (SEQ ID NO 29):
QNMHCQYILS LLLLSLNVVF FAAGDSLDSV DDKSRRCTDE

QTEVCAKTEC KAEDAAMTEL LLEGESDITE HPDFVYYTRC

MQRCCAKLNG AKVAPLKEEE KRRGPTKLPF QSIFDVADQQ

TVERCDATMC KSQRMKYESL VARTTSYKKL RASQELRDYK

ECIESCDAKL NGRQ

A preferred peptide derived from the amino acid sequence of the 21 kDa excretory/secretory antigen is:

SEQ ID NO 30:
KSQRMKYESL VARTTSYKKL R

*Trichinella pseudospiralis* 28 kDa excretory/
secretory protein (SEQ ID NO 31):
MVHFKVMNIN ITLLFAIILL QFISNASTER FRKLKKESMP

AAVKEHLKKL MKNSIVQQSG HESEGGIVEE TKQVLQKSHD

SFYHLEGTIH KLEEKLEKEK KLYDPWDKKD NSAKRLALGF

FVRVAKQYRE GLLNESGMMA GIRQPRKKCF VKYSMLDEYS

ATTEEDDKIL MKIERKFYKC ESQCQSNTKM KDFYTKDLCI

LKCFEKKLDK FAEKLGVPFD EAKVNEGVNQ LQDLDKSVVP

FTSI

A preferred peptide having an amino acid sequence of the 21 kDa excretory/secretory antigen is:

SEQ ID NO 32:
EKKLDKFAEK LGVPFDEAKV N

BRIEF DESCRIPTION OF THE DRAWINGS

The sequences of the peptides indicated above and their position relative to the full sequences of the antigenic *Trichinella* proteins are illustrated by figures. Further figures show the results of tests performed on the peptides with respect to their properties to discriminate between negative and positive sera:

FIG. 1 shows the sequence of *Trichinella spiralis* newborn larvae-specific protein SS1 (SEQ ID NO 1). The sequences (SEQ IDs NO 2 and 3) shown in italics relate to preferred peptides which can be used in the diagnostic composition according to the invention.

FIG. 2 shows the sequence of *Trichinella spiralis* newborn larvae-specific protein SS2 (SEQ ID NO 4). The sequences (SEQ IDs NO 5-9) shown in italics relate to preferred peptides which can be used in the diagnostic composition according to the invention.

FIG. 3 shows the sequence of *Trichinella spiralis* glutamic acid-rich protein cNBL1700 (SEQ ID NO 10). The sequences (SEQ IDs NO 11 and 12) shown in italics relate to preferred peptides which can be used in the diagnostic composition according to the invention.

FIG. 4 shows the sequence of *Trichinella spiralis* 43 kDa secreted glycoprotein (SEQ ID NO 13). The sequences (SEQ IDs NO 14-17) shown in italics relate to preferred peptides which can be used in the diagnostic composition according to the invention.

FIG. 5 shows the sequence of *Trichinella spiralis* 53 kDa excretory/secretory antigen (SEQ ID NO 18). The sequences (SEQ IDs NO 19-28) shown in italics relate to preferred peptides which can be used in the diagnostic composition according to the invention.

FIG. 6 shows the sequence of *Trichinella pseudospiralis* 21 kDa excretory/secretory protein (SEQ ID NO 29). The sequence (SEQ ID NO 30) shown in italics relates to a preferred peptide which can be used in the diagnostic composition according to the invention.

FIG. 7 shows the sequence of *Trichinella pseudospiralis* 28 kDa excretory/secretory protein (SEQ ID NO 31). The sequence (SEQ ID NO 32) shown in italics relates to a preferred peptide which can be used in the diagnostic composition according to the invention.

DETAILED DESCRIPTION OF THE INVENTION

Figure 8A:
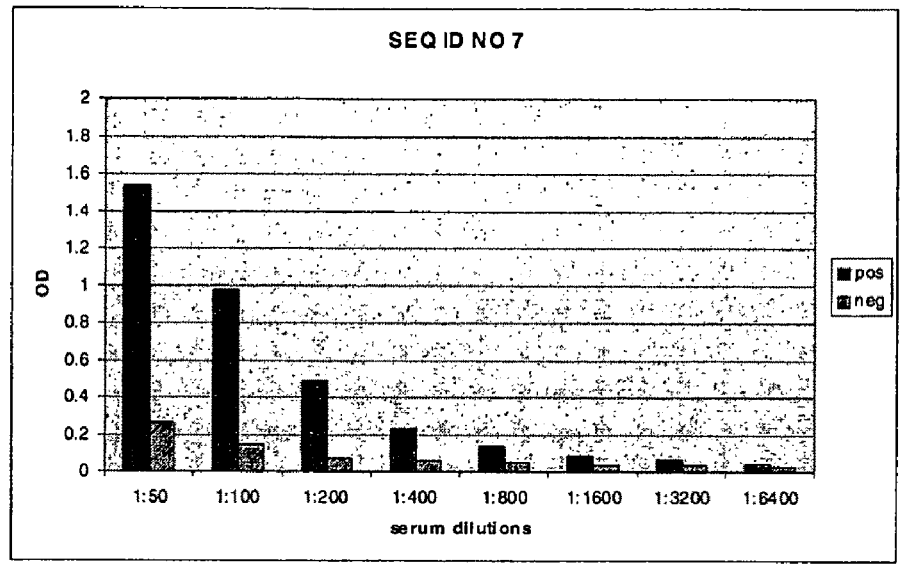
FIGS. 8a and b show the results of 2 of the preferred SS2 peptides (SEQ IDs NO 7 and 8) tested in ELISA assays. It was shown that both peptides are able to discriminate between negative and positive sera. Serial two fold dilutions of the serum sample were tested.
Figure 8B:
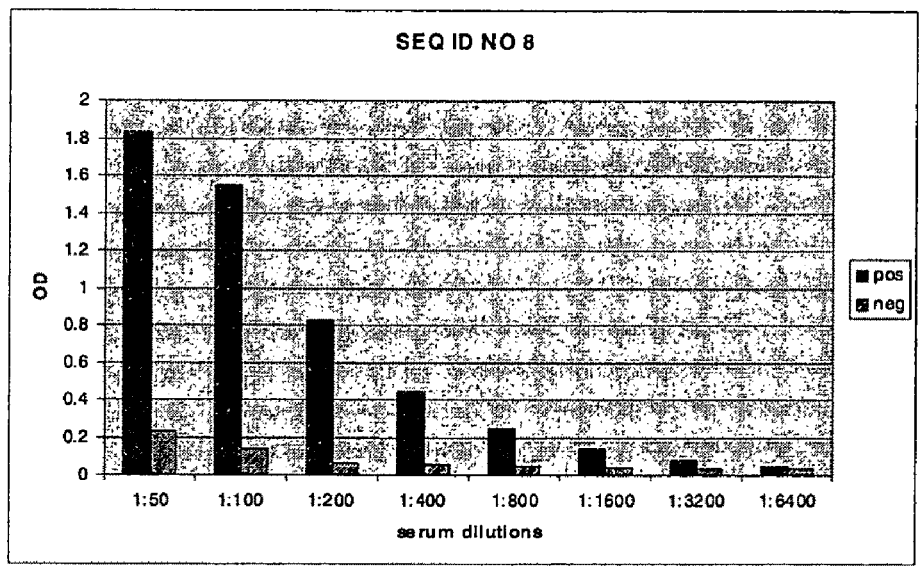

Diagnostic compositions according to the invention can e.g. be employed in usual immunoassays in which the at least one peptide of the composition is reacted with antibodies possibly present in a sample obtained from an animal or a human. In case antibodies are present an immune complex is formed which can be detected by methods known in the art. As stated above the invention does not only cover diagnostic compositions but also especially immunoassay methods in which the compositions are used as antigenic substance.

On basis of the compositions according to the invention containing one or more of the peptides diagnostic tests can be designed which allow individual animal/carcass testing in a more rapid, standardized and automatic manner than currently used digestion methods. The tests allow full documentation with a short time to result and internal controls will show the reliability of the test procedure. It will be suitable for low and high throughput testing with little equipment required. Since the same sample (serum/meat juice) can be used for other diagnostic tests (e.g. for Salmonellosis in pigs), the sampling efficiency can be increased.

The diagnostic tests used with the invention are immunological assay systems which quantitatively or qualitatively detect the presence of antibodies in samples taken from animals or human and preferably allow the determination of a status with regard to *Trichinella* infection. Preferably the peptides including the amino acid sequences that are identified as epitopes of *Trichinella* antigenic proteins are synthesized or made by recombinant techniques.

The assay system can be either a homogeneous type of immunoassay or a heterogeneous type of an immunoassay.

Heterogeneous immunoassays involve binding of the at least one peptide either as a mixture or covalently linked to a solid support. In this embodiment the sample containing the antibodies is brought into contact with the peptide(s) and the bound antibodies are detected with a second antibody which is specific to the species from which the first antibody originates and is conjugated with an enzyme to allow detection by means of a chemical reaction.

Homogeneous assays use at least one peptide as probe for the detection of antibodies in solution. In this aspect of the invention, the peptides are e.g. chemically directly or indirectly via a chemical linker linked with fluorescent dyes and can be used either as mixture or covalently linked as tracers in a fluorescent assay system.

In a particularly preferred embodiment of the invention said method is a fluorescence polarization assay to detect antibodies in a sample by contacting said sample with the tracer molecule, allowing the mixture to interact for a certain period of time and then measuring the polarization value which indicates whether antibodies were present in the sample fluid.

The invention is not limited to the mentioned polarisation assays. Further methods which can be applied as well are e.g. immunoblot techniques, ELISA, RIA, SPR (surface plasmon resonance) or agglutination assays to list only some examples.

One main advantage of the invention is that the peptides selected for the compositions or methods due to their limited length can be easily linked to further peptides or immobilised or incorporated into tracer molecules for special test systems. A further advantage is that the peptides can be selected from different antigens present at different stages of the infection cycle which allows the design of tests with a broad diagnostic window if desired.

E.g. it is possible to provide a composition including at least one peptide corresponding to an amino acid sequence from new-born larvae specific antigenic proteins such as e.g. the SS1, SS2 (Niu et al. 2005) protein or NBL1700 antigen (Zarlenga et al. 2002).

Such compositions allow detection of antibodies in the early stage of infection of an organism with *Trichinella* and thus overcome current limitations of serologic methods to detect antibodies in the sera within the first 15 days following infection by the parasite.

If later stages of the infection are to be detected one can use a composition containing a peptide including a series of amino acids that form a continuous or discontinuous epitope recognized by sera from pigs infected with *Trichinella*. Especially preferred are compositions containing peptides corresponding to an epitope of one of the following ES-antigen components: 43 kDa, 53 kDa, 28 kDa and 21 kDa.

As stated above the selection of peptides as diagnostic antigens provides a number of advantages over the use of whole antigens. One advantage is that the peptides used according to the invention in general are much shorter compared to the whole antigens. The risk of cross-reactions etc. is diminished and it is no problem to combine 2 or more different peptides in a composition as is provided by a preferred embodiment of the invention. By using different peptides one can optimise the test systems with respect to selectivity etc.

It is possible to include peptides in the composition in form of a mixture. Especially preferred is to provide the peptides in form of a fusion peptide or fusion peptides.

A further preferred embodiment provides that the composition includes peptides corresponding to epitopes of different antigens which are expressed by *Trichinella* at different stages of the infection's cycle. As stated above this embodiment allows the design of test systems with a broad diagnostic window. Such test systems may at the same time detect early and late infections.

One further embodiment of the invention intended for heterogeneous assays provides a composition wherein at least one peptide or fusion peptide is linked to solid support.

Independent on the form of the assay a further embodiment provides that the composition includes a tracer complex composed of at least one peptide or fusion peptide linked to a marker.

As a rule the peptide or fusion peptide is linked with a marker via a linker and it is especially preferred that the marker whether bound directly or via a linker to the peptide or fusion peptide respectively is a fluorophore.

The use of fluorescence polarisation assay is a preferred option and in this context a further preferred embodiment of the invention provides that the tracer complex composed of peptide or fusion peptide respectively with a fluorophore is adapted to such fluorescence polarisation assay.

In this context an especially preferred embodiment provides that the linker linking the peptide or fusion peptide to the marker is adapted to reduce or inhibit rotation of the marker relative to the peptide or fusion peptide. By this embodiment the so called propeller-effect which often negatively influences the result of fluorescence polarisation assays can be avoided or reduced. The propeller-effect and its implications for the preparation of fluorescent probes is described in 'The Handbook—A Guide to Fluorescent Probes and Labeling Technologies Invitrogen Corp., 10$^{th}$ edition, Richard P. Haugland, ISBN 0-9710636-4-8.

In a preferred embodiment of the invention, linkers which contain amino acids with sterically bulky side chains such as phenylalanin, tyrosin or tryptophan or with side chains that reduce the rotational freedom of the peptide chain when incorporated into a oligopeptide such a proline or histidine are used. In a particularly preferred embodiment of the invention, linkers which contain one or several amino acids with tryptophan as side chains are used.

A general model how to reduce the "propeller effect" is lined out in Example 1.

Table 2 referred to under Example lists a number of tracer complexes consisting of a peptide and a marker which can be used with the invention in fluorescence polarisation assay.

The invention is not only directed to a composition but also to a method for the diagnosis of *Trichinella* infection.

The method according to the invention comprises in vitro-detection of antibodies against at least one peptide from *Trichinella* in a tissue sample taken from an animal or a human. As a rule the sample is contacted with diagnostic compositions according to the invention. The presence of antibodies in the sample is detected by testing whether or not a binding reaction of antibodies in the sample with the immunogenic peptide in the diagnostic composition has occurred.

It is possible to detect the binding reaction by homogenous assays like ELISA, immunoblot techniques, RIA etc. or by heterogeneous assays.

Especially preferred is a homogenous assay in form of a fluorescence polarisation assay.

The tissue sample analysed can be taken from an animal selected from a group comprising mammals and reptiles, including specifically swine, wild boars, equines, carnivores, aquatic animals, bear, fox, marten, sheep, cattle and from humans.

The tissue used as sample is selected from body fluids including blood, serum, plasma and urine, saliva and as far as animals are concerned also from meat juice, carcasses and meat.

The invention further covers specific peptides including fusion peptides and tracer complexes made from the peptides and a marker.

Finally the invention covers kits for the diagnosis of a *Trichinella* infection in a sample taken from a susceptible animal or human, which comprise the diagnostic composition according to the invention together with the necessary reagents to perform a usual homogenous or heterogeneous immunoassay to detect antibodies against the at least one peptide included in the composition.

EXAMPLES

Example 1

Development of a Labelling Strategy Using a Model Peptide

The FLAG peptide (a well known tag, e.g. used for immuno affinity purification) was used as a model peptide to develop a labelling strategy for peptide tracers which allows chemical linking of a fluorophore to the peptide to reduce or inhibit rotation of the fluorophore relative to the peptide. The FLAG peptide and an elongated FLAG peptide were used to and coupled to 5-Carboxyfluorescein (5-CF) with a linker containing the following amino acid composition:

```
                                              (SEQ ID NO 33)
FLAG:  Asp-Tyr-Lys-Asp-Asp-Asp-Asp-Lys (SEQ ID NO 34)
Gly(9)-FLAG:  Gly(9)-Asp-Tyr-Lys-Asp-Asp-Asp-
Asp-Lys (SEQ ID NO 34)
5-CF-Gly(9)-FLAG:  5-CF-Gly(9)-Asp-Tyr-Lys-Asp-
Asp-Asp-Asp-Lys (SEQ ID NO 35)
5-CF-Pro-Gly(9)-FLAG:  5-CF-Pro-Gly(9)-Asp-Tyr-
Lys-Asp-Asp-Asp-Asp-Lys (SEQ ID NO 36)
5-CF-Trp-Gly(9)-FLAG:  5-CF-Trp-Gly(9)-Asp-Tyr-
Lys-Asp-Asp-Asp-Asp-Lys (SEQ ID NO 37)
5-CF-Trp(2)-Gly(9)-FLAG:  5-CF-Trp(2)-Gly(9)-Asp-
Tyr-Lys-Asp-Asp-Asp-Asp-Lys
```

FPA analysis of the FLAG Model peptide shown in Table 1 was performed by the following procedure.

The FLAG Model peptide tracers were diluted in TBS (containing 25 mM Tris, 0.15M NaCl, NP40 0.05%, pH 7.2) at a concentration of 8.1 nM or 2.7 nM, respectively in a single well of a black colored 96-well plate. The plate was incubated for 2 minutes at room temperature on an orbital shaker set at 1350 rpm and then incubated for another minute without shaking. Blank measurement of the sample was then performed by reading the fluorescence polarisation in a fluorescence reader (Safir2, Tecan, Switzerland) with excitation and emission wavelength set at 470 nm and 520 nm, respectively.

Then, 1, 3 or 10 molar equivalence of the anti-FLAG M2 monoclonal antibody (Sigma, Switzerland), respectively, were added and the plate was incubated at room temperature with shaking (1350 rpm) for 3 minutes and then for an additional minute without shaking. Then the plate was measured.

The mP values were calculated according to the following formula:

$$mP = \frac{(\text{parallel light} - \text{perpendicular light})}{(\text{parallel light} + \text{perpendicular light})} * 1000$$

The ΔmP values were obtained by subtracting the mP values of the negative serum from the positive sera:

$$\Delta mP = mP_{positive\ serum} - mP_{negative\ serum}$$

TABLE 1

|  |  | 5-CF-Pro-Gly$_{(9)}$-FLAG | | 5-CF-Trp-Gly$_{(9)}$-FLAG | | 5-CF-Trp$_{(2)}$-Gly$_{(9)}$-FLAG | |
|---|---|---|---|---|---|---|---|
| ΔmP values | | 8.1 nM | 2.7 nM | 8.1 nM | 2.7 nM | 8.1 nM | 2.7 nM |
| anti-FLAG antibody | 10 equiva- | 62 | 33 | 86 | 55 | 124 | 97 |
|  | 3 equiva- | 33 | 15 | 50 | 27 | 78 | 35 |
|  | 1 equiva- | 14 | 5 | 19 | 9 | 37 | 5 |

The labelled FLAG peptides show the influence of the bulky amino acids in the linker. The amino acids Trp-Trp in the linker resulted in higher ΔmP values than one Trp or one Pro and therefore showing a higher hindrance of the rotation of the fluorophore due to the bulky amino acids.

Example 2

Discrimination Between *Trichinella* Positive and *Trichinella* Negative Serum in FPA Using Different Peptides According to the Invention Table 2 depicts for some of the *Trichinella* peptides their ability to discriminate between a *Trichinella* positive and a *Trichinella* negative serum sample using fluorescence polarisation assay (FPA). Shown are the DmP values of the tracers and the buffer composition which resulted in DmP values=20 mP.

FPA analysis of the tracers shown in Table 2 was performed by the following procedure. A 15 ml aliquot of the positive or negative serum was diluted with 185 ml of buffer (PBS with detergent as indicated in Table 2) in a single well of a black coloured 96-well plate. The plate was incubated for 2 minutes at room temperature on an orbital shaker set at 1350 rpm and then incubated for another minute without shaking. Blank measurement of the sample was then performed by reading the fluorescence polarisation in a fluorescence reader (Safire2, Tecan, Switzerland) with excitation and emission wavelength set at 470 nm and 520 nm, respectively. Then, 5 ml tracer was added to the reaction mixture to a final concentration of 5 nM and the plate was incubated at room temperature with shaking (1350 rpm) for 15 minutes and then for an additional minute without shaking. Then the plate was measured.

The mP values were calculated according to the following formula:

$$mP = \frac{(\text{parallel light} - \text{perpendicular light})}{(\text{parallel light} + \text{perpendicular light})} * 1000$$

The ΔmP values were obtained by subtracting the mP values of the negative serum from the positive sera:

$$\Delta mP = mP_{positive\ serum} - mP_{negative\ serum}$$

Example 3

Discrimination Between *Trichinella* positive and *Trichinella* Negative Serum in Elisa Assays Using SS2 Peptides SEQ ID NO 7 and 8

Single wells of a 96-well microtitre plate were coated with the SS2 peptides (SEQ ID No 5 and 6) at a concentration of 10 mg ml-1 in carbonate buffer 0.1 M (pH 9.5) overnight at 4° C. The plate was washed 4 times with 0.05% Tween 80 and then blocked with a PBS buffer containing 2% I-block and 0.1% Tween 20 for 90 minutes at 25° C.±3° C. Pig sera were diluted 50-fold in phosphate buffered saline and serial 2-fold dilutions were incubated in the microtitre plate with shaking (500 rpm) for 2 hours at room temperature. The plates were washed

TABLE 2

| Tracer | Sequence | Buffer | ΔmP |
|---|---|---|---|
| SEQ ID NO 5 | MHKITHKSIV SRHTFAVYLL VSGQK | PBS with 0.05% Glucopyranosid | 39 |
| SEQ ID NO 6 | VGGTDVRPHSH PWQIQLLKSET G | PBS with 0.1% Sarcosyl | 35 |
| SEQ ID NO 7 | LSTASRPTNP YTGSRPTSPS SGSRP | PBS with 0.1% Sarcosyl | 20 |
| SEQ ID NO 8 | PTYPSSGSRP TYPSSGSRPT YPYTG | PBS with 0.001% Pluronic | 66 |
| SEQ ID NO 9 | PTYPSSGSRP TYPSSGSRP | PBS with 0.001% Pluronic | 66 |
| SEQ ID NO 16 | VVYSKTSSSR LEMYGSF | PBS | 20 |
| SEQ ID NO 19 | QNERQFDENK LKKLLKPLGK LYKTPSD | PBS with 0.05% DOC | 33 |
| SEQ ID NO 20 | QNERQFDENK LKKLLKPLG | PBS with 0.05% Chaps | 28 |
| SEQ ID NO 23 | NNYRGRQGIA GLGML | PBS with 0.003% Triton X-100 | 23 |
| SEQ ID NO 24 | VVTIFRKNGK TTEVLSL | PBS with 0.1% Sarcosyl | 57 |
| SEQ ID NO 26 | KPFGDEIDRI LRKAF | PBS with 0.05% Glucopyranosid | 31 |
| SEQ ID NO 27 | KEADKSALRL KRFAKPPKGF F | PBS with 0.02% SDS | 31 |
| SEQ ID NO 28 | ALRLKRFAK | PBS with 0.02% SDS | 41 |

4 times with 0.05% Tween 80 Detection of the bound antibodies was performed by incubation with a goat anti-pig IgG(Fc)-POD conjugate (Bethyl Laboratories, USA) at a concentration of 1.3 ug/ml for 1 h at RT with shaking (500 rpm). Following four more washes, 2'-azino-bis(3-ethylbenzthiazoline-6-sulphonic acid) (ABTS) substrate solution was added and incubated for 30 minutes, colour development was measured in a ELISA reader (Tecan, Switzerland) at a wavelength of 405 nm.

Example 4

Discrimination Between *Trichinella* positive and *Trichinella* Negative Serum in FPA Using Tracer Complexes Including Peptides SEQ ID NO 14 and 24

Figure 9A:
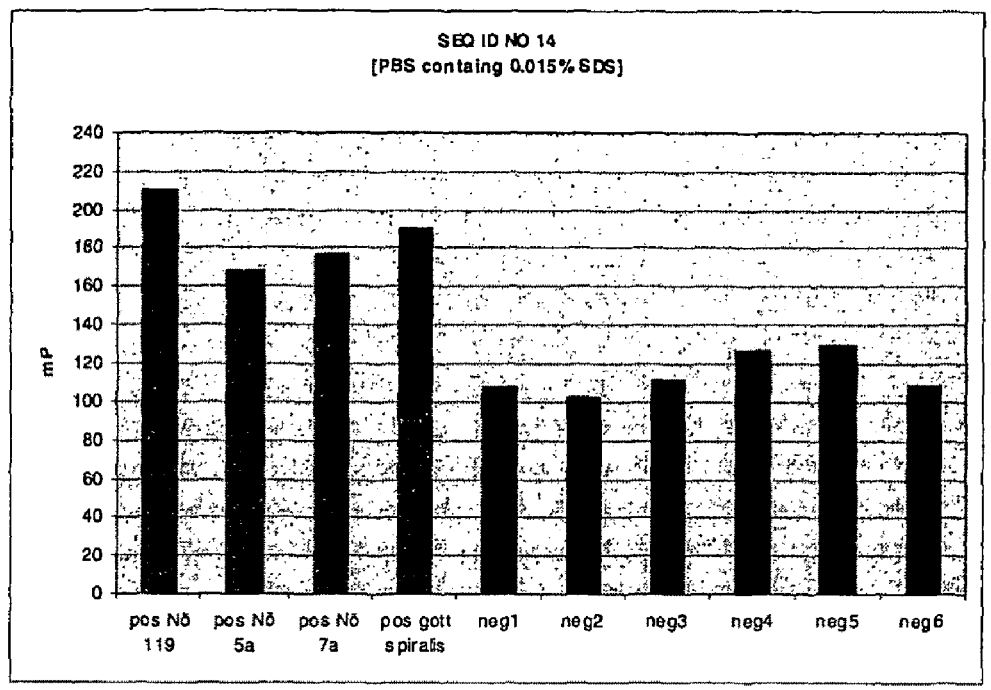
FIGS. 9a and b show the results of a FPA of 2 peptides (SEQ ID NO 14 (9a); SEQ ID NO 24 (FIG. 9b).
Figure 9B:
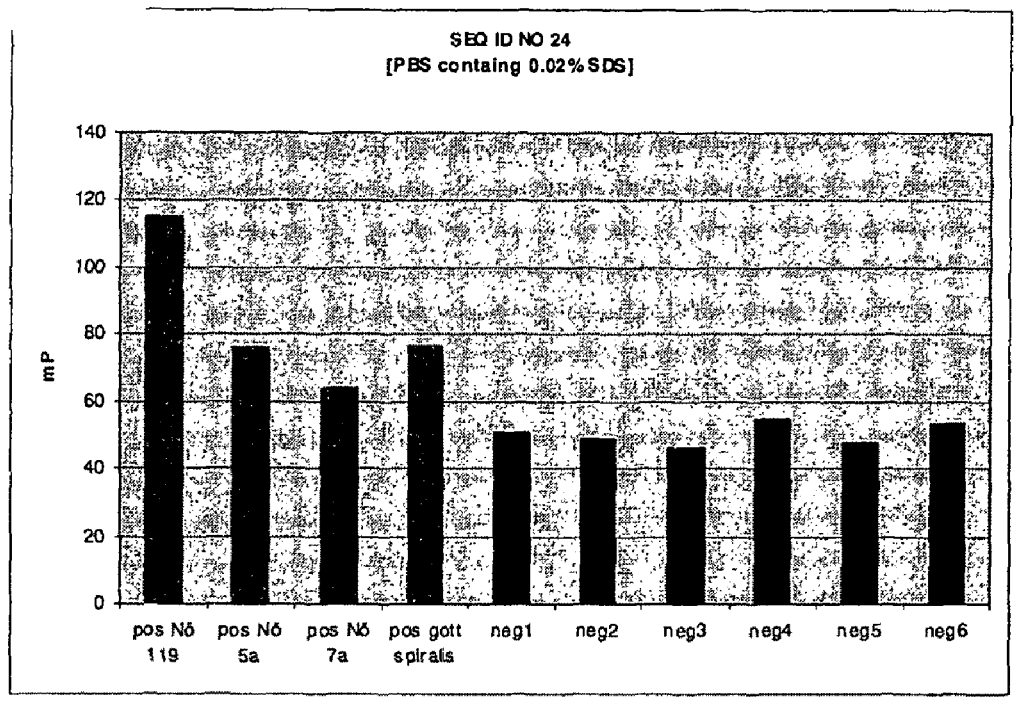

FPA analysis of the tracers shown in FIGS. 9a and 9b was performed by the following procedure. A 15 ml aliquot of the positive or negative serum was diluted with 185 ml of buffer (PBS with 0.02% sodium dodecyl sulphate (SDS)) in a single well of a black coloured 96-well plate. The plate was incubated for 2 minutes at room temperature on an orbital shaker set at 1350 rpm and then incubated for another minute without shaking. Blank measurement of the sample was then performed by reading the fluorescence polarisation in a fluorescence reader (Safire2, Tecan, Switzerland) with excitation and emission wavelength set at 470 nm and 520 nm, respectively. Then, 5 ml tracer was added to the reaction mixture to a final concentration of 5 nM and the plate was incubated at room temperature with shaking (1350 rpm) for 3 minutes and then for an additional minute without shaking. Then the plate was measured.

The mP values were calculated according to the following formula:

$$mP = \frac{(\text{parallel light} - \text{perpendicular light})}{(\text{parallel light} + \text{perpendicular light})} * 1000$$

The $\Delta$mp values were obtained by subtracting the mP values of the negative serum from the positive sera:

$$\Delta mP = mP_{positive\ serum} - mP_{negative\ serum}$$

The invention claimed is:

1. A diagnostic composition comprising at least one peptide consisting of a peptide selected from the group consisting of:
   a peptide according to SEQ ID NO: 2;
   a peptide according to SEQ ID NO: 3;
   a peptide according to SEQ ID NO: 5;
   a peptide according to SEQ ID NO: 6;
   a peptide according to SEQ ID NO: 7;
   a peptide according to SEQ ID NO: 8;
   a peptide according to SEQ ID NO: 9;
   a peptide according to SEQ ID NO: 11;
   a peptide according to SEQ ID NO: 12;
   a peptide according to SEQ ID NO: 14;
   a peptide according to SEQ ID NO: 15;
   a peptide according to SEQ ID NO: 16;
   a peptide according to SEQ ID NO: 19;
   a peptide according to SEQ ID NO: 20;
   a peptide according to SEQ ID NO: 21;
   a peptide according to SEQ ID NO: 22;
   a peptide according to SEQ ID NO: 23;
   a peptide according to SEQ ID NO: 24;
   a peptide according to SEQ ID NO: 25;
   a peptide according to SEQ ID NO: 26;
   a peptide according to SEQ ID NO: 27;
   a peptide according to SEQ ID NO: 28;
   a peptide according to SEQ ID NO: 30;
   and a peptide according to SEQ ID NO: 32.

2. The diagnostic composition according to claim 1, wherein the composition includes at least two peptides selected from the group.

3. The diagnostic composition according to claim 2, wherein the at least two peptides are included in the composition in a form of a mixture.

4. The diagnostic composition according to claim 2, wherein the peptides are fused.

5. The diagnostic composition according to claim 2, wherein the at least two peptides contain epitopes of different antigens from *Trichinella* expressed at different stages of the infection cycle.

6. The diagnostic composition according to claim 1, wherein the at least one peptide is linked to a solid support.

7. A method for the diagnosis of a *Trichinella* infection in a susceptible animal or human being, the method comprising:
   taking a body fluid from the animal or human being;
   contacting the body fluid with the diagnostic composition according to claim 1; and
   detecting, in vitro, whether antibodies against at least one peptide from *Trichinella*
   are present in the body fluid by testing whether or not a binding reaction of antibodies in the body fluid with the at least one peptide selected from the group in the diagnostic composition has occurred.

8. The method according to claim 7, wherein the animal is selected from a group consisting of mammals and reptiles.

9. The method according to claim 7, wherein the binding reaction is detected by a homogenous assay.

10. The method according to claim 9, wherein the homogenous assay is a fluorescence polarization assay.

11. A kit for the diagnosis of a *Trichinella* infection in a sample taken from a susceptible animal or human being, which comprises the diagnostic composition according to claim 1.

12. A diagnostic composition comprising a tracer complex comprising at least one peptide linked to a marker, wherein the at least one peptide consists of a peptide selected from the group consisting of:
   a peptide according to SEQ ID NO: 2;
   a peptide according to SEQ ID NO: 3;
   a peptide according to SEQ ID NO: 5;
   a peptide according to SEQ ID NO: 6;
   a peptide according to SEQ ID NO: 7;
   a peptide according to SEQ ID NO: 8;
   a peptide according to SEQ ID NO: 9;
   a peptide according to SEQ ID NO: 11;
   a peptide according to SEQ ID NO: 12;
   a peptide according to SEQ ID NO: 14;
   a peptide according to SEQ ID NO: 15;
   a peptide according to SEQ ID NO: 16;
   a peptide according to SEQ ID NO: 19;
   a peptide according to SEQ ID NO: 20;
   a peptide according to SEQ ID NO: 21;
   a peptide according to SEQ ID NO: 22;
   a peptide according to SEQ ID NO: 23;
   a peptide according to SEQ ID NO: 24;
   a peptide according to SEQ ID NO: 25;
   a peptide according to SEQ ID NO: 26;
   a peptide according to SEQ ID NO: 27;
   a peptide according to SEQ ID NO: 28;
   a peptide according to SEQ ID NO: 30;
   and a peptide according to SEQ ID NO: 32.

13. The diagnostic composition according to claim 12, wherein the at least one peptide selected from the group in the tracer complex is linked to the marker via a linker.

14. The diagnostic composition according to claim 12, wherein the marker is a fluorophore.

15. The diagnostic composition according to claim 12, wherein the tracer complex is adapted to a fluorescence polarization assay.

16. The diagnostic composition according to claim 12, wherein the at least one peptide selected from the group is linked to the marker via a linker, which reduces or inhibits rotation of the marker relative to the linked peptide.

17. The diagnostic composition according to claim 16, wherein the linker is composed of one or more bulky molecules, which reduce or inhibit rotation of the marker relative to the linked peptide.

18. The diagnostic composition according to claim 16, wherein the linker is composed of one or more bulky amino acids, which reduce or inhibit rotation of the marker relative to the linked peptide.

19. The diagnostic composition according to claim 18, wherein the linker is an amino-acid linker having the sequence Trp-Trp.

20. The diagnostic composition according to claim 18, wherein the linker is an amino-acid linker containing 1 to 3 prolines.

* * * * *